US012605066B2

(12) United States Patent
Siminou et al.

(10) Patent No.: US 12,605,066 B2
(45) Date of Patent: Apr. 21, 2026

(54) METHODS, SYSTEMS, AND DEVICES FOR MONITORING ANISOCORIA AND ASYMMETRY OF PUPILLARY REACTION TO STIMULUS

(71) Applicant: Neuroptics, Inc., Irvine, CA (US)

(72) Inventors: Kamran Siminou, Newport Coast, CA (US); Claudio Privitera, San Clemente, CA (US)

(73) Assignee: Neuroptics, Inc., Irvine, CA (US)

( * ) Notice: Subject to any disclaimer, the term of this patent is extended or adjusted under 35 U.S.C. 154(b) by 0 days.

(21) Appl. No.: 17/955,675

(22) Filed: Sep. 29, 2022

(65) Prior Publication Data

US 2023/0013271 A1     Jan. 19, 2023

Related U.S. Application Data

(63) Continuation of application No. 15/930,301, filed on May 12, 2020, now Pat. No. 11,484,197, which is a continuation of application No. 16/183,786, filed on Nov. 8, 2018, now Pat. No. 10,687,702, which is a continuation of application No. 14/953,134, filed on Nov. 27, 2015, now Pat. No. 10,154,783, which is a (Continued)

(51) Int. Cl.
| | |
|---|---|
| *A61B 3/11* | (2006.01) |
| *A61B 3/00* | (2006.01) |
| *A61B 3/14* | (2006.01) |

(52) U.S. Cl.
CPC ............ *A61B 3/112* (2013.01); *A61B 3/0025* (2013.01); *A61B 3/0058* (2013.01); *A61B 3/14* (2013.01)

(58) Field of Classification Search
CPC ......... A61B 3/112; A61B 3/0025; A61B 3/14; A61B 3/11; A61B 3/0058; A61B 3/145; A61B 3/0091; A61B 3/113; A61B 2560/0431; A61B 3/0041; A61B 5/031; A61B 3/0083; A61B 5/1103; A61B 5/1128; A61B 5/4064; A61B 5/4076; A61B 5/4836; A61B 5/4845; A61B 5/7264; A61B 3/185; A61B 17/02; A61B 3/0008; A61B 3/0033; A61B 3/0075; A61B 3/024; G16H 30/40; G16H 40/63; G16H 50/20
See application file for complete search history.

(56) References Cited

U.S. PATENT DOCUMENTS

| | | | |
|---|---|---|---|
| 2006/0030760 A1* | 2/2006 | Geiger .................. | A61B 3/112 |
| | | | 351/205 |
| 2006/0215113 A1* | 9/2006 | Chernyak ............... | A61B 3/11 |
| | | | 351/205 |

FOREIGN PATENT DOCUMENTS

| | | | | |
|---|---|---|---|---|
| CA | 2602299 | * | 9/2006 | ............... A61B 3/11 |
| WO | WO 2006/032920 | * | 3/2006 | ............... A61B 3/11 |

* cited by examiner

*Primary Examiner* — Brandi N Thomas
(74) *Attorney, Agent, or Firm* — Hybrid Law Group P.C.

(57) ABSTRACT

A computer program is disclosed for performing the following method: recording images of a response of a left pupil to a stimulus thereby resulting in a first set of sequential images; recording images of a response of a right pupil to the same stimulus at the same time as the first images were recorded, thereby resulting in a second set of sequential images; displaying on a display simultaneously the first set of images and the second set of image, wherein the two sets of images are synchronized, and wherein a center of the left pupil of each image from the first set of sequential images is aligned with a center of the right pupil from the second set of sequential images on the display.

3 Claims, 8 Drawing Sheets

Related U.S. Application Data continuation of application No. 13/929,795, filed on Jun. 28, 2013, now Pat. No. 9,198,570, which is a continuation of application No. 13/149,926, filed on Jun. 1, 2011, now Pat. No. 8,534,840, which is a continuation of application No. 12/626,452, filed on Nov. 25, 2009, now Pat. No. 7,967,442.

(60) Provisional application No. 61/118,541, filed on Nov. 28, 2008.

ID: 0                    Right Eye
180uW @ 667ms   2000/01/01  01:11:39

MAX     MIN          CON    LAT
2.8     2.2          -21%   0.23
ACV     MCV          ADV    T75
-1.56   -2.70        0.42   1.9

— Time of 75% Recovery
   After Constriction

— Average Dilation Velocity

— Max and Min Pupil Diameter

— Duration of Light Stimulation

— Latency of the Pupil Constriction Onset

Hold down the          Release the LEFT        Keep the Pupillometer
LEFT Button            Button when ready       in position. Press LEFT
                                               again to abort

FIG. 4A              FIG. 4B             FIG. 4C

Playing...

METHODS, SYSTEMS, AND DEVICES FOR MONITORING ANISOCORIA AND ASYMMETRY OF PUPILLARY REACTION TO STIMULUS

PRIORITY

This is a continuation of U.S. patent application Ser. No. 15/930,301, filed May 12, 2020, which is a continuation of U.S. application Ser. No. 16/183,786, now U.S. Pat. No. 10,687,702, filed Nov. 8, 2018, which is a continuation of U.S. application Ser. No. 14/953,134, now U.S. Pat. No. 10,154,783, filed Nov. 27, 2015, which is a continuation of U.S. application Ser. No. 13/929,795, now U.S. Pat. No. 9,198,570, filed Jun. 28, 2013, which is a continuation of U.S. patent application Ser. No. 13/149,926, now U.S. Pat. No. 8,534,840, filed Jun. 1, 2011, which is a continuation of U.S. patent application Ser. No. 12/626,452, filed Nov. 25, 2009, now U.S. Pat. No. 7,967,442, which claims priority from U.S. Provisional Patent Application Ser. No. 61/118, 541, filed on Nov. 28, 2008, the entire disclosures of which are incorporated by reference herein.

TECHNICAL FIELD OF THE DISCLOSURE

The present disclosure relates to methods, systems and devices or instruments for monitoring anisocoria and asymmetry of reaction to stimulus between the left and right pupil of a subject, sometimes referred to herein as a "patient" or an "individual". The methods and systems can be implemented through devices and instruments such as Pupillometers, which are high-tech instruments that are currently used to obtain information about a pupil's response to a stimulus. Examples of such Pupillometers are described in detail in U.S. Pat. Nos. 6,116,736, 6,260,968, 6,820,979, and 7,147, 327, all of which are incorporated herein by reference in their entirety. Examples of Pupillometers in commercial use include the ForeSite™ Pupillometer, the NPi-™ 100 Pupillometer, the PLR-100™ Pupillometer, the DP1000™ Pupillometer, and the A-1000™ Pupillometer, all made by Neuroptics®, and all incorporated herein by reference in their entirety. These types of pupillometers can be used on human or animal subjects.

BACKGROUND OF THE DISCLOSURE

Systems for monitoring pupil size and pupil responsiveness characteristics are well known in the art and are generally referred to as pupillometry systems or, simply, pupillometers. One early Pupillometer is described in U.S. Pat. No. 3,533,683, which issued to Stark et al. on Oct. 13, 1970 and is entitled "Dynamic Pupillometers Using Television Camera System" (incorporated herein by reference). The Stark et al. system employed a television camera system, a digital computer system, an infrared light source, and a visual light stimulator for determining the instantaneous size of a pupil as an eye (or neurologic pupillary control system) of a patient was exposed to various stimuli.

More advanced hand-held pupillometers are now commercially available and can be used in many applications including critical care, anesthesiology, research, and refractive surgery and ophthalmology. One example is the PLR-100™ Pupillometer by Neuroptics®. The PLR-100™ pupillometer is a hand-held and cordless device which measures pupil size and dynamics. It can be used for either a static pupil measurement protocol (i.e., reporting pupil size measurements such as weighted average pupil size and standard deviation) as well as a dynamic pupil measurement protocol (i.e., reporting pupil light reflex measurements including: maximum pupil size before constriction, minimum pupil size after constriction, percent constriction, average constriction velocity, maximum constriction velocity, dilation velocity and time to reach 75% of the initial maximum pupil size after the constriction). The user can adjust the light stimulus intensity and duration. Numerical results are displayed on a color LCD numerically and graphically. Measurements may also be printed to a portable printer via infrared (wirelessly) transmission.

One area of pupillary clinical diagnosis and monitoring that has gained increased attention over the years is detecting and monitoring differences in size and asymmetry in pupillary response to stimulus between the left and right pupils. This condition where the sizes of the left and right pupils of an individual at rest are unequal is called anisocoria. A variety of potential causes for anisocoria exist, ranging from trivial or normal variation, to life threatening conditions, such as increased intracranial pressure (ICP) and brain swelling from a head injury, uncal herniation, lesions, and aneurismal compression. In general all those neurological conditions affecting the efferent pathway of the pupil system starting from the oculomotor nuclei in the midbrain up to the pupil sphincter muscle can be a cause of anisocoria.

Asymmetry in pupillary response is when the left and right pupils respond to a stimulus, such as a light stimulus, in different ways that go beyond the definition of anisocoria. For example, the pupil size between the left and right pupils at rest may be the same or very close in size, but the two pupils may react to a stimulus very differently, such as having different maximum pupil size before constriction, minimum pupil size after constriction, percent constriction, average constriction velocity, maximum constriction velocity, dilation velocity and time to reach 75% of the initial maximum pupil size after the constriction. Like anisocoria, asymmetry in pupillary response may also be indicative of an underlying medical condition.

Because anisocoria and asymmetry in pupillary response may be symptoms in some cases of very serious and immediately life threatening conditions, it is important for medical practitioners to have tools for easy, quick and convenient ways to accurately detect, measure, and view in real-time differences in pupillary size and pupillary reaction to stimulus between the right and left pupils. There are, unfortunately, very few such tools presently available. Thus, there is a need for high-tech instruments that can perform such functions. The methods, systems and devices of the present disclosure meet this and other such needs in the art.

SUMMARY OF THE DISCLOSURE

In one embodiment, a Pupillometer is disclosed. The Pupillometer has a display, an imaging apparatus that has a pupil finder and a microprocessor, and a memory in communication with the microprocessor. The display is sized to simultaneously display a video of y or more seconds in length of a left pupil and a video of y or more seconds in length of a right pupil. The pupil finder identifies the perimeter of a pupil. The imaging apparatus is capable of recording images of an individual's pupils at a rate of x image frames per second for a period of y or more seconds and playing back said image frames as a video at x image frames per second or at another rate that is faster or slower than x image frames per second. The memory has stored therein a program for enabling said microprocessor to do the following: (i) identify a center of the left pupil and a center of the right pupil for each image frame; (ii) synchronize each image frame of the two videos starting from the first frame; (iii) cause the display to display the two videos simultaneously such that each of the image frames of the video of the left eye is synchronized to a corresponding image frame of the video of the right eye when played back on the display; and (iv) cause the two videos to be displayed so that the center of the left pupil in each image frame is aligned on the display with the center of the right pupil for the corresponding image frame.

In another embodiment, a method for monitoring asymmetry in response to a stimulus between a left pupil and a right pupil of an individual is disclosed. The method includes the following steps: recording for a period of time y at a rate of x image frames per second a response of a left pupil to the stimulus thereby resulting in a first set of sequential image frames; recording for the same period of time y at the same rate of x image frames per second a response of a right pupil to the stimulus thereby resulting in a second set of sequential image frames; and displaying on a display simultaneously the first set of image frames of the response of the left pupil to the stimulus and the second set of image frames of the response of the right pupil to the stimulus. The two sets of image frames are synchronized per frame starting from the first frame for each set, and a center of the left pupil is aligned with a center of the right pupil on the display.

In another embodiment, a program product comprising a computer-readable medium and computer-executable instructions recorded on the computer-readable medium for performing a method is disclosed. The method comprises: recording for a period of time y at a rate of x image frames per second a response of a left pupil to the stimulus thereby resulting in a first set of sequential image frames; recording for the same period of time y at the same rate of x image frames per second a response of a right pupil to the stimulus thereby resulting in a second set of sequential image frames; displaying on a display simultaneously the first set of image frames of the response of the left pupil to the stimulus and the second set of image frames of the response of the right pupil to the stimulus. The two digital sets of image frames are synchronized per frame starting from the first frame for each set, and a center of the left pupil is aligned with a center of the right pupil on the display.

Other features and advantages will be apparent from the following description of the various embodiments of the disclosure, which illustrate, by way of example, the principles of the disclosed devices and methods.

BRIEF DESCRIPTION OF THE DRAWINGS

According to common practice, the various features of the drawings may not be presented to scale. Rather, the dimensions of the various features may be arbitrarily expanded or reduced for clarity. Included in the drawings are the following figures:

FIGS. 4A-4C depict the steps taken by the handler of the Pupillometer depicted in FIG. 1 in order to take pupillary measurements.

DETAILED DESCRIPTION

Figure 1:
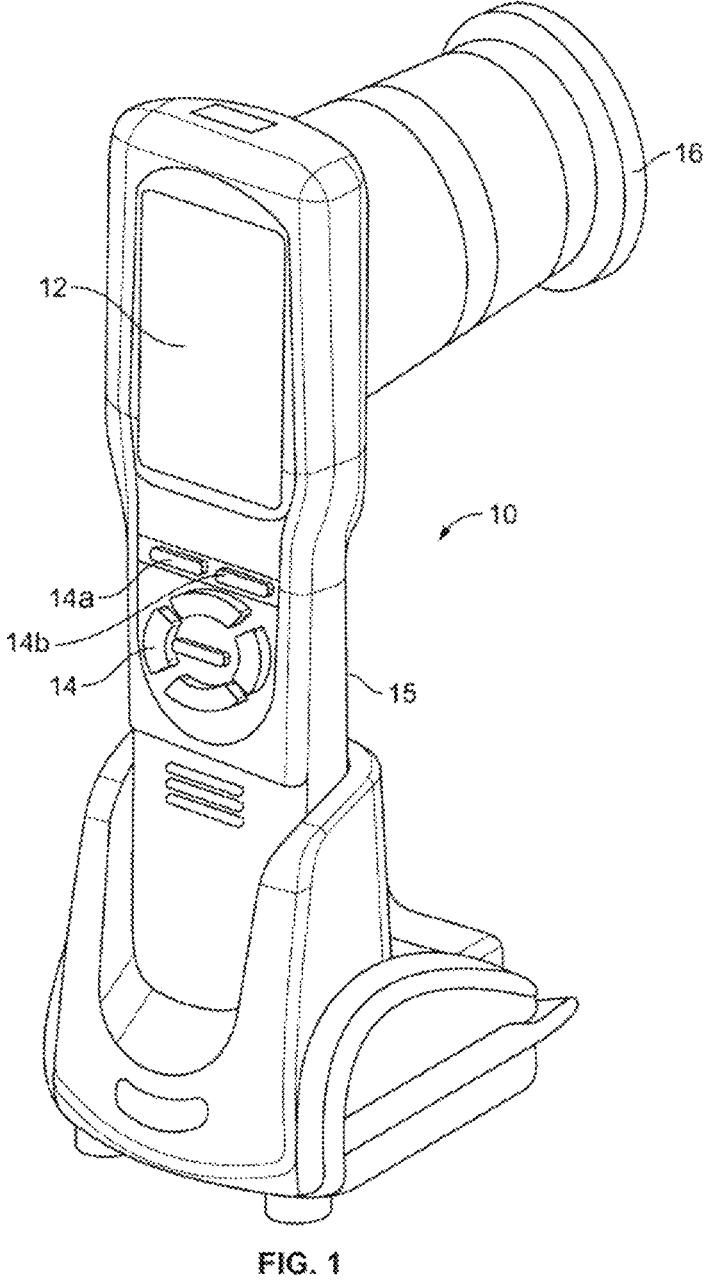
FIG. 1 is an illustration of a Pupillometer having a display in accordance with one embodiment.

Disclosed herein is a pupillary analysis system that includes a pupillometer, such as the one shown in FIG. 1, with features that enable it to monitor and compare in real-time the response of an individual's left and right pupils to a stimulus, such as a light stimulus, auditory stimulus, or noxious stimulus. In the examples described herein the pupillometer has a light stimulus source built into it. Variations on the type of stimulus and the arrangement of that stimulus in relation to the pupillometer, such as those variations described in U.S. Pat. No. 7,147,327, are also contemplated and incorporated herein by reference. The working components, electronics, and software, other than those described below, are also fully described in, e.g., U.S. Pat. No. 7,147,327, and will therefore not be further discussed herein.

Before the present subject matter is further described, it is to be understood that the subject matter described herein is not limited to the particular embodiments described, and as such may of course vary. It is also to be understood that the terminology used here in is for the purpose of describing particular exemplary embodiments only, and is not intended to be limiting in any fashion, and in particular to the doctrine of equivalents. Unless defined otherwise, all technical terms used herein have the same meaning as commonly understood by one skilled in the art to which this subject matter belongs.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the subject matter described herein. The upper and lower limits of these smaller ranges may independently be included in the smaller ranges, and are also encompassed within the subject matter described herein, subject to any specifically excluded limit in the stated range. Where the stated range includes one or both of the limits, ranges excluding either or both of those included limits are also included in the subject matter described herein.

It must be noted that as used herein and in the appended claims, the singular forms "a," "and," and "the" include plural referents unless the context clearly dictates otherwise.

FIG. 1 depicts a handheld pupillometer, such as that described in U.S. Pat. No. 7,147,327. Pupillometer 10 includes a display 12, handle 15 for gripping the pupillometer while using it, and headrest 16. Headrest 16 is used to position the pupillometer 10 optimally to take measurements of the pupils of an individual's eyes. U.S. Pat. No. 7,216,985, which is incorporated herein by reference in its entirety, describes headrests of the type that may be used with pupillometer 10. Pupillometer 10 also includes a keypad 14, including various control buttons including buttons 14a and 14b, which are used to operate the pupillometer 10.

Pupillometer 10 operates essentially as a handheld optical scanner. In one embodiment, it stimulates the eye of an individual with a flash of light and captures and analyzes a rapid sequence of digital images to obtain a temporal measurement of the diameter of the individual's pupil. The intensity and duration of the light stimulus can be set by the user of pupillometer 10 using the controls in the keypad 14. In one embodiment, maximum light strength is approximately 180 µW and maximum duration is approximately 800 ms. Pupillometer 10 can acquire images using a self-contained infrared illumination source and a digital camera. It analyzes the captured image data and displays a summary of the measurement in the display 12, which can be an LCD display. Data may also be printed out on an optional thermal printer or downloaded to an external computer via an infrared port (IrDA) or transmitted via USB port and cable to a computer. Pupillometer 10 can use a menu driven graphical user interface with a color LCD screen 12 for data display. A keypad 14 completes the user interface and enables manual entry of individual subject identification (ID) numbers and other information.

Pupillometer 10 can be powered by any number of power sources known to those of skill in the art. In one embodiment it is powered by a 4.2 volt rechargeable lithium ion battery.

Pupillary data sampled at approximately ten frames per second (10 fps)(or less), approximately twenty frames per second (20 fps), approximately thirty frames per second (30 fps), approximately forty frames per second (40 fps), approximately fifty frames per second (50 fps), or more and for a total duration of up to about 3600 seconds (i.e., about 60 minutes) can be used in the calculation of a number of different pupillary reaction variables that can be displayed numerically or graphically on the display 12 at the end of each measurement. In one embodiment, the Pupillometer 10 takes one measurement of a pupil by sampling thirty frames per second (30 fps) for three seconds to acquire a total of approximately ninety sequential images of a pupil's response to a stimulus. Pupillometer 10 can sample data at anywhere between about 1 frame per second (1 fps) (or less) to about one hundred frames per second (100 fps) (or more) for any length of time between about one (1) second (or less) and about 3600 seconds (i.e., about 60 minutes).

Pupillometer 10 has internal memory large enough to store three hundred or more measurements. All measurement data contained in Pupillometer's 10 memory can be downloaded to an external computer or laptop, such as a Window® based computer or laptop or computer or laptop with a different operating system. Measurement data can be encrypted and contained in a file named with the date and time of the moment of the download and extention "dat". For example, R_20080909_1030.dat would indicate a file downloaded on Sep. 9, 2008 at 10:30. Previous measurements and data can be browsed, retrieved and printed using the keypad controls 14 and appropriate menus displayed in the screen display 12.

Figure 2:
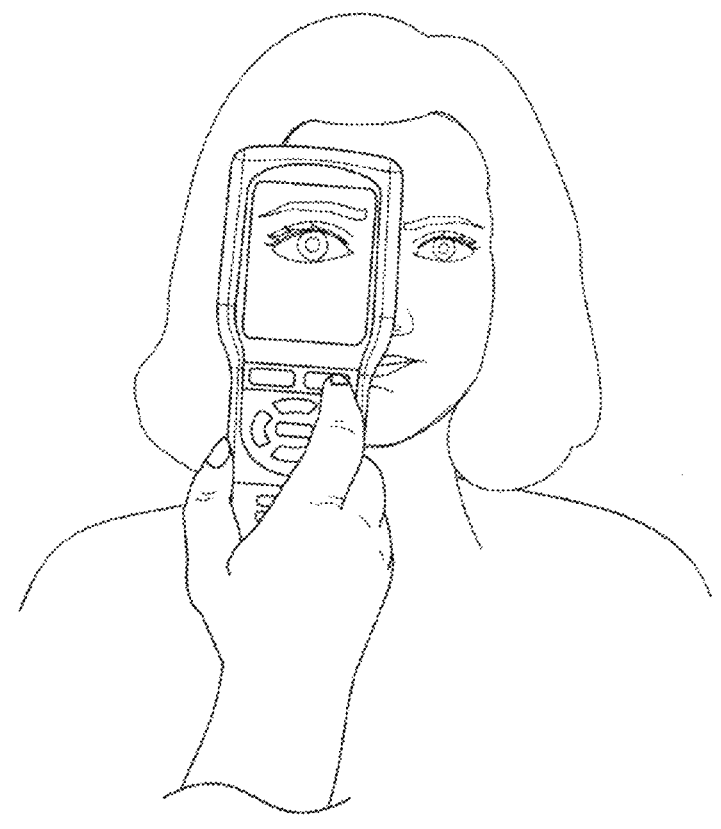
FIG. 2 is an illustration of the Pupillometer depicted in Figure one being used to take a measurement of the pupil of a right eye of an individual in response to a visual light stimulus.

FIG. 2 shows pupillometer 10 being used to take a measurement of the pupil of a right eye of an individual in response to a visual light stimulus. As shown, the operator of pupillometer 10 positions pupillometer 10 at a right angle to the individual's axis of vision and does not tilt pupillometer. The headrest 16 can be used to provide optimum positioning of pupillometer 10 relative to the eye being analyzed.

Pupillary measurements can be divided into three phases as shown in FIGS. 4A-4C. Pressing either one of the buttons 14a (for the right pupil) or 14b (for the left pupil) on the keypad 14 can activate the first phase, i.e., the targeting phase of pupillometer 10. By pressing key 14a, pupillometer 10 automatically saves the data as left eye data, and by pressing key 14b, pupillometer 10 automatically saves the data as right eye data. In one embodiment, the operator of pupillometer 10 holds down button 14a or 14b during the targeting phase while keeping pupillometer 10 snuggly up to the subject's eye. During the targeting phase, a video image of the eye is displayed in the LCD window as shown in FIG. 2 and FIG. 4A. The subject's pupil must be centered within the field of view as shown in FIGS. 2 and 4A.

During phase 2 of pupillary measurement, pupillometer 10 has a pupil finder that automatically detects the pupil 20 and marks it with a perimeter 25 drawn around the perimeter of the pupil 20. Algorithms and software for detecting a pupil and drawing a perimeter around it are known in the art. For example, U.S. Pat. No. 7,147,327, describes various imaging processing procedures and methods that can be used to do that. The perimeter 25 can be any color that is easy to visualize, such as green, white, red, etc. From the beginning of phase 1 until now, the operator has been holding down the button 14a or 14b.

Once the pupil finder of pupillometer 10 has found the pupil 20 and has marked it with the perimeter 25, the operator can now release the button 14a or 14b. Release of the button 14a or 14b initiates the third phase, which is the actual measurement phase. In the measurement phase, pupillometer 10 subject's the individual's eye to a flash of light applied at time 0.0 seconds. In other words the flash of light is applied at the same instant as the first image of the pupil is being recorded. The flash of light can also be applied just before or just after the pupillometer begins recording images of the pupil. As discussed above, the intensity and duration of the flash of light can be controlled by the operator. FIG. 4C shows an image on the display 12 of pupillometer 10 of the pupil as it is being recorded during the measurement phase. The pupillometer may also be set to operate without the flash of light, such that measurements are taken of a pupil that has not been stimulated but is at rest. When the comparison of the left and right pupil is made for measurements that don't involve a stimulus, the videos of the right and left pupil are synchronized in the same manner as when measurements are taken after a stimulus.

Figure 3:
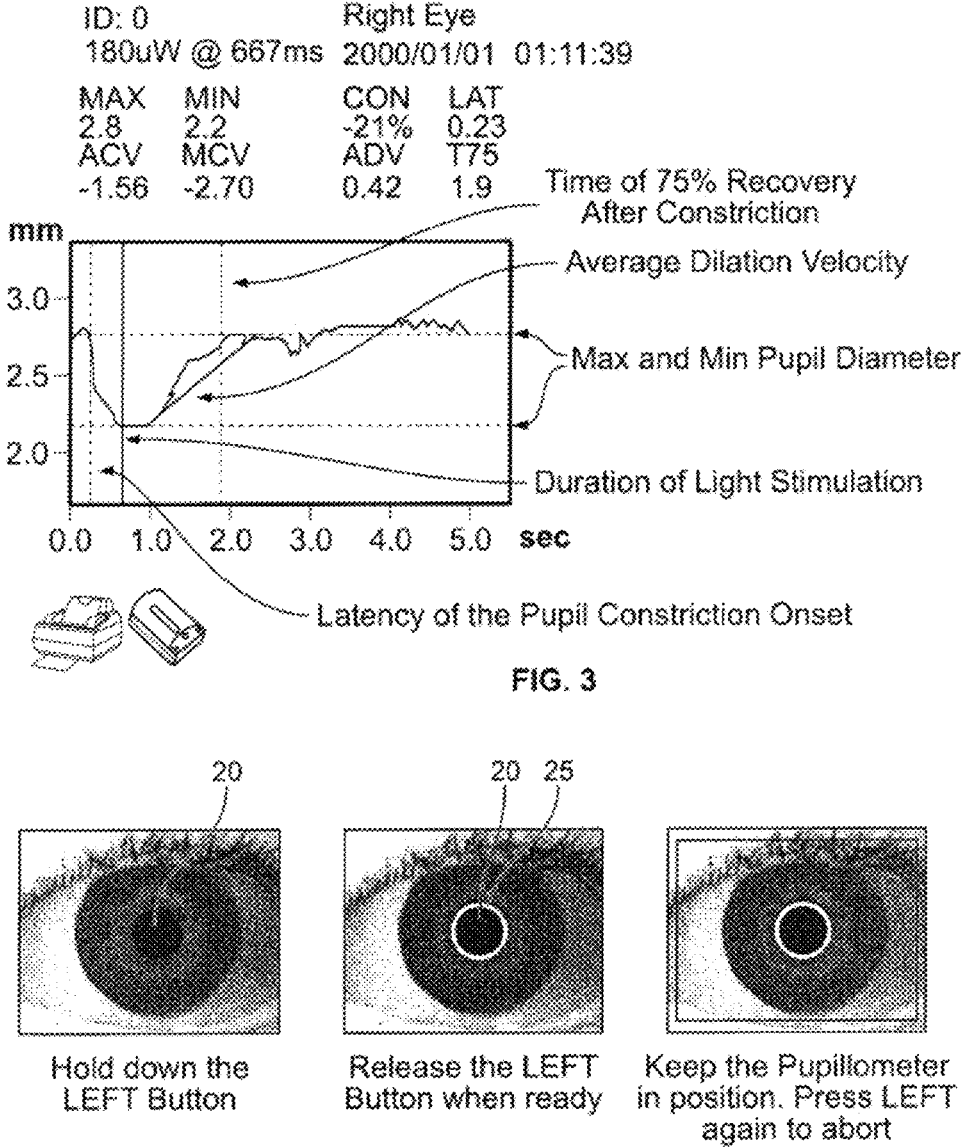
FIG. 3 shows a screen shot of the display of the Pupillometer depicted in FIG. 1 showing results of a measurement of a pupil of an individual in response to a visual light stimulus.

FIG. 3 shows a screen shot of the display 12 of pupillometer 10 showing a results page that includes various measurements of the pupil that was subjected to the light stimulus and recorded during phases 1-3 described above. The results page can show a plot of the pupil response and can, for example, report the following information:

ID, the identification code of the subject measured (for example 0 in FIG. 3); which eye was measured (right in the example in FIG. 3), and the date and time of the measurement. If the measurement was affected by certain problems during phases 1-3, the data shown in the results page may be in a special color, such as red, to indicate that there was a problem. Some examples of problems that can occur during measurement are excessive eye blinks or excessive pupillometer motion.

The intensity and duration of the light stimulation. In the example shown in FIG. 3, the light stimulation intensity was 180 micro Watts for a toal duration of 667 milliseconds. The duration of the light stimulation is also represented by a colored vertical line superimposed over the pupil plot (0.0 seconds is always the onset of the light stimulation).

MAX and MIN represent the diameter of the pupil before the constriction (MAX=2.8 mm in this example) and just at the peak of the constriction (MIN=2.2 mm in this example), respectively in FIG. 3. These measurements are given in millimeters and are represented by two horizontal gray lines superimposed over the pupil plot. The variable CON is the percent of the constriction (MAX-MIN)/MAX as a percent.

LAT is the latency and it represents the amount of time it takes before the onset of pupillary constriction in response to the light stimulus. It is given in seconds (for example 0.23 seconds in the FIG. 3) and is represented by a vertical colored line, different from the color of the light stimulation duration line, superimposed over the pupil plot.

ACV and MCV are the average and the maximum constriction velocity and they are given in millimeters/second, respectively. The negative sign differentiates the constriction from the opposite papillary movement that is dilation. Both velocities refer to the constricting movement of the pupil diameter responding to the flash of light.

ADV is the dilation velocity (given in millimeters/second) and represents the average papillary velocity, when, after having reached the peak of the constriction, the pupil tends to recover and to dilate back to its initial resting size. Pupillary recovery after a light reflex constriction is usually characterized by an initial and more rapid phase followed by a much slower converging movement. The dilation velocity reported here refers to the initial and stronger recovery and is indicated in the graph in FIG. 3 by a line fit to the corresponding dilation phase of the pupil profile.

T75 is the total time taken by the pupil to constrict and then to return to 75% of the initial resting pupil size. It is given in seconds and is represented by a vertical colored line superimposed on the pupil plot in a color that is different than the other lines that are superimposed on the pupil plot.

The above describes operation of pupillometer 10 with respect to each measurement of a pupil that is taken. When taking a measurement of a pupil, the operator uses the keypad 14 to enter various data regarding the pupil. That data can include, e.g., the identity of the individual whose pupil it is. As discussed above, pupillometer 10 memory stores that information and can use it to perform direct comparisons between the response of the left eye and the response of the right eye to the flash of light applied by pupillometer 10. Which pupil of the individual is being measured is specified by the keypad buttons 14a and 14b. If the user presses keypad button 14a then the pupillometer automatically stores the pupillary measurement as left eye data, and if the user presses keypad button 14b then the pupillometer automatically stores the pupillary measurement data as right eye data.

In one embodiment, pupillometer 10 has the following components that enable it to perform a comparison between the left and right eyes of the individual. Pupillometer 10 has a display 12 that is sized to simultaneously display a video of y or more seconds in length of a left pupil and a video of y or more seconds in length of a right pupil of the same individual. The lengths of each video can be anywhere from 1 second or less to sixty or more minutes. Pupillometer 10 has an imaging apparatus that includes a pupil finder that identifies the perimeter of a pupil and a microprocessor. The imaging apparatus is capable of recording images of an individual's pupils at a rate of x frames per second for a period of y or more seconds and playing back said images as a video at x frames per second or at another rate that is faster or slower than x frames per second. As explained above, in one embodiment, the imaging apparatus records or samples the images at a rate of approximately 30 fps for a period of approximately 3.0 seconds. The playback mechanism of pupillometer 10 can play the videos back on display 12 at 30 fps, or at a different rate controlled by the user using the keypad 14 to control the playback rate. The playback mechanism can also pause the video playback or it can fast-forward or rewind the video playback at various speeds controlled by the user using the keypad 14 controls, which can include pause, rewind, fast-forward and video playback, fast-forward and rewind speed buttons and/or functions. For example, the user can view the images one image set at a time and can control how long he or she wants to view the image set before manually forwarding or advancing to the next set of images or rewinding to the previous set of images. This can be done to compare the right pupil to the left pupil image set by image by set for each set of images taken during the procedure. The user can pause as long as he or she wants at a particular set of images to, for example, compare the difference between the right pupil and the left pupil in that set of images.

Pupillometer 10 also has a memory in communication with the microprocessor. The memory has stored therein a pupil comparison program. The pupil comparison program can include a pupil finder as described above. The pupil comparison program enables the microprocessor to perform the following functions:

(i) identify a center of the left pupil and a center of the right pupil for each image frame;

(ii) synchronize each frame of the two videos starting from the first frame;

(iii) cause the display to display the two videos simultaneously such that each of the frames of the video of the left eye is synchronized to a corresponding frame of the video of the right eye when played back on the display;

(iv) cause the two videos to be displayed so that the center of the left pupil in each frame is aligned on the display with the center of the right pupil for the corresponding frame.

Figure 5:
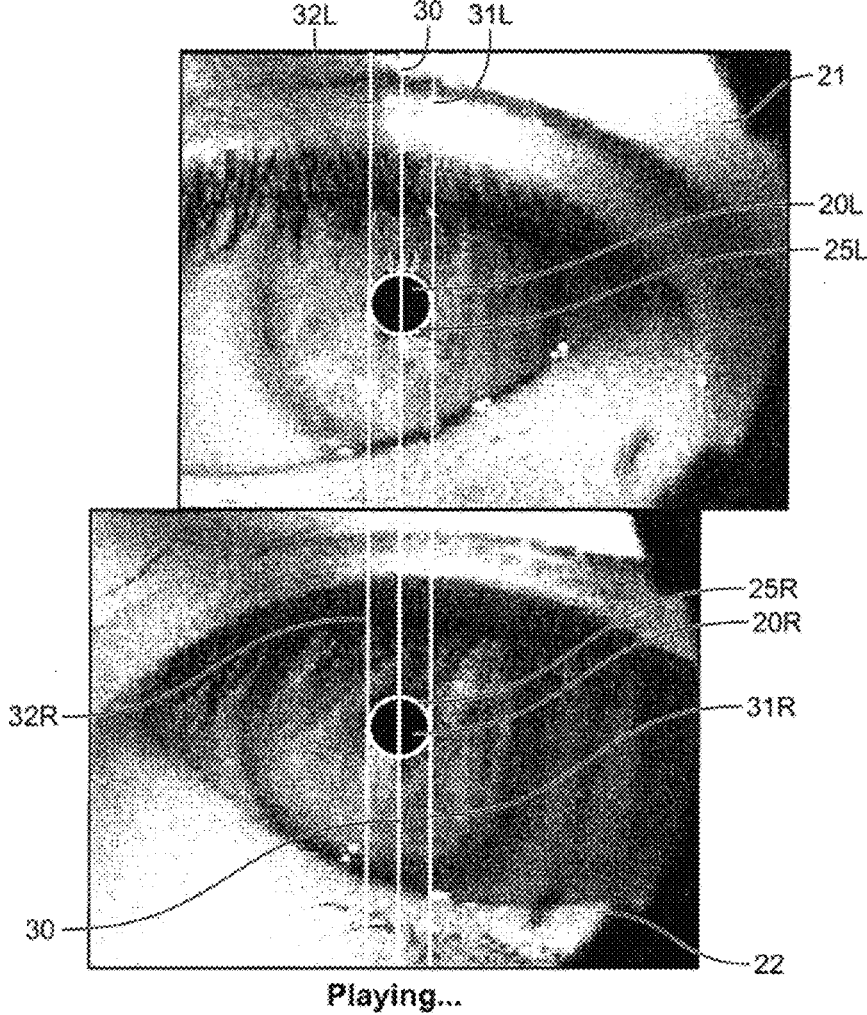
FIG. 5 shows a screen shot of the display of the Pupillometer depicted in FIG. 1 showing the left and right pupils of an individual aligned during video playback of pupillary response to a light stimulus.

FIG. 5 shows one example of a pupillometer display 12 showing an image frame 21 of a left pupil 20L recorded during measurement of the pupil as described above, and an image frame 22 of a right pupil 20R recorded during measurement of the pupil as described above. Image frame 21 is part of a series of sequential image frames of the left pupil recorded at a rate of x frames per second and which together form a video of y seconds in length. In one embodiment, x is approximately 30 and y is approximately 3.0. In other embodiments, x can be about 10 (or less), about 20, about 40, about 50 or more and y can be 1, 2, 4, 5 or up to 3600 or more, and in general x can be between about 1 (or less) and about 100 frames (or more) per second, and y can be any length of time between about one (1) second and 3600 seconds (i.e., 60 minutes) (or more). Image frame 22 is part of a series of sequential image frames of the right pupil recorded at the same rate of x frames per second and which together form a video of y seconds in length, which is the same length as the video associated with image frame 21.

Thus, in one embodiment, there are approximately 90 image frames for the video of the left pupil and 90 image frames for the video of the right pupil. Each image frame of the video of the left pupil has a corresponding image frame in time in the video of the right pupil. For example, image frame 1 of the left pupil and image frame 1 of the right pupil are both taken at the exact same amount of time after onset of the flash of light from pupillometer 10 (alternatively, image frame 1 can be taken just before or just after onset of the flash of light). Thus, image frame 1 of the left pupil and image frame 1 of the right pupil are corresponding image frames. Likewise, image frame 2 of the left pupil and image frame 2 of the right pupil are both taken at the exact same amount of time after onset of the flash of light from pupillometer 10 (or from onset of video recording without a flash of light). Alternatively, image frame 2 of each pupil can be taken just before or just after onset of the flash of light. Thus, image frame 2 of the left pupil and image frame 2 of the right pupil are corresponding image frames, and so on and so forth for approximately 90 images that when played back at 30 fps form a video that lasts about 3 seconds. In the example shown in FIG. 5, image frame 21 is the 24th image of the left eye taken by pupillometer 10, which means that it is taken at 800 milliseconds after onset of the flash of light from pupillometer 10 (or from onset of video recording without a flash of light). Likewise, image frame 22 is the $24^{th}$ image of the right eye taken by pupillometer 10, which means that it too is taken at 800 milliseconds after onset of the flash of light from pupillometer 10 (or from onset of video recording without a flash of light).

It should be understood that with respect to all embodiments described herein, the first image of each pupil can be taken just before, simultaneously with, or just after the onset of the flash of light. Thus, for example, the first image of each pupil can be taken within one, two, three, four, five, six, seven, eight, nine or more milliseconds up to one second before or after the onset of the flash of light. It can also be taken simultaneously with the flash of light. In one embodiment, the first image of each pupil is taken 500 milliseconds before the onset of the flash of light.

As shown in FIG. 5, the pupil comparison program enables the microprocessor to determine the center of each pupil and to draw a straight line 30 that runs through the center of each pupil. That way pupils 20L (left pupil) and 20R (right pupil) are lined up with one another on the display. Pupil centering programs are known in the art and some are described in U.S. Pat. No. 7,147,327. FIG. 5 shows just one frame of each pupillary measurement of the left pupil 20L being lined up with its corresponding pupillary measurement frame of the right pupil 20R, but each frame of the pupillary measurement of the left pupil 20L is lined up with its corresponding pupillary measurement frame of the right pupil on the display 12. Thus, when the two videos are played back on the display 12 simultaneously, it is easy to see the difference in response of the left pupil relative to the right pupil. One of the reasons why it is so important to align and center the two pupils in the video playback mode is to compensate for eye movement so that the operator can easily compare one eye to the other.

The pupil comparison program provides another feature that makes it even easier to follow the difference in the pupillary responses of the left and right pupil. The pupil comparison program enables the microprocessor to draw a pair of parallel straight lines that extend from the perimeter of the left pupil to the perimeter of the right pupil in each image frame. As shown in FIG. 5, the parallel lines have a first section 32L/31L and a second section 32R/31R, wherein in the first section 32L/31L the distance between the parallel lines is defined by the diameter of the left pupil 20L for each frame, and in the second section the distance between the parallel lines 32R/31R is defined by the diameter of the right pupil 20R for each frame. The diameter of the left pupil 20L is defined by the pupil perimeter 25L, which is established by pupillometer 10 using its pupil finder. The diameter of the right pupil 20R is defined by the pupil perimeter 25R, which is likewise established by pupillometer 10 using its pupil finder. In order to further make it easier to visualize the difference in response between the left and right eyes, the first section lines 32L/31L can be a different color than the second section lines 32R/31R. For examples parallel lines 32L/31L can be red while parallel lines 32R/31R can be green.

Figure 6:
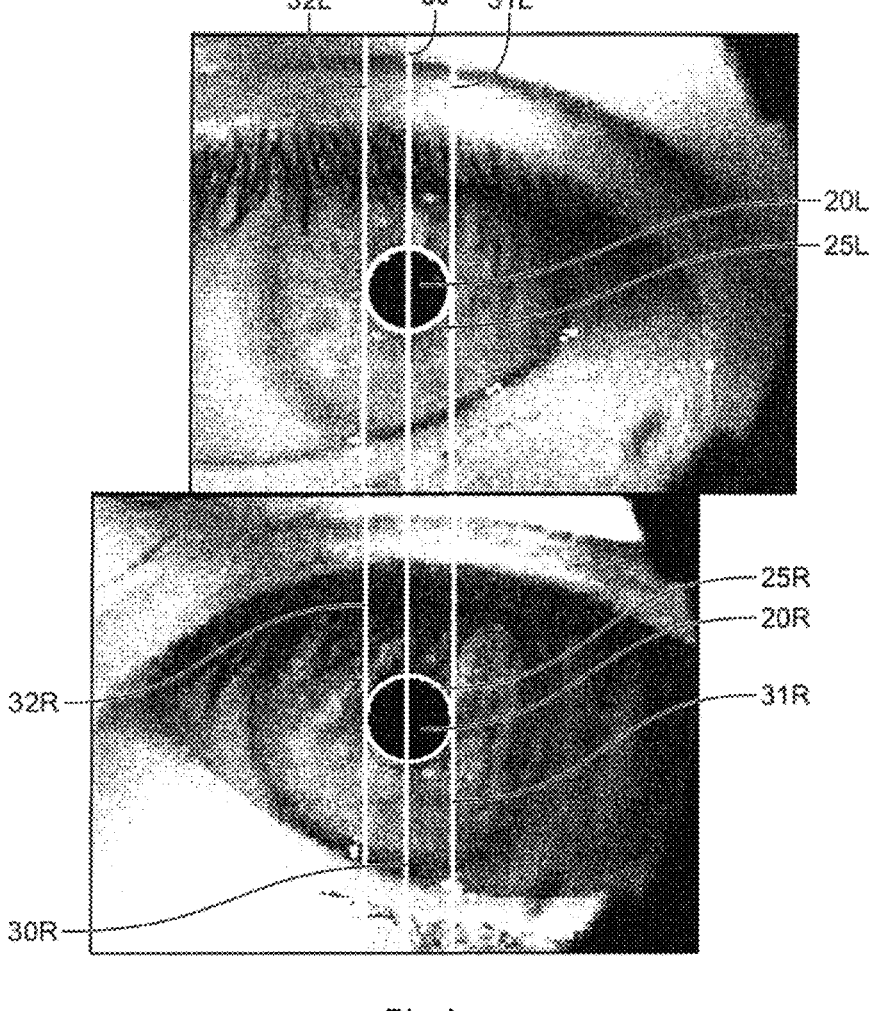
FIG. 6 shows second screen shot from the same video described with respect to FIG. 5.

FIG. 6 shows the $72^{nd}$ image frame of each video of each eye, which means that each frame was taken at 2.4 seconds after onset of the flash of light of pupillometer 10. At 2.4 seconds after onset of the flash of light, the pupils 20L and 20R have dilated back to their resting position. Looking at the still images in FIGS. 5 and 6, it would appear that there is very little pupil size asymmetricity in this individual. But for a better understanding, one would view the video comparing the two sets of images at 30 fps or perhaps at a slower speed such as 10 fps to get a much clearer view of whether or not there is substantial anisocoria or asymmetry in pupillary response to light stimulus. The pairing of parallel lines 32L/31L with 32R/31R makes it very clear whether there is anisocoria or asymmetry in papillary response to light stimulus.

Figure 7:
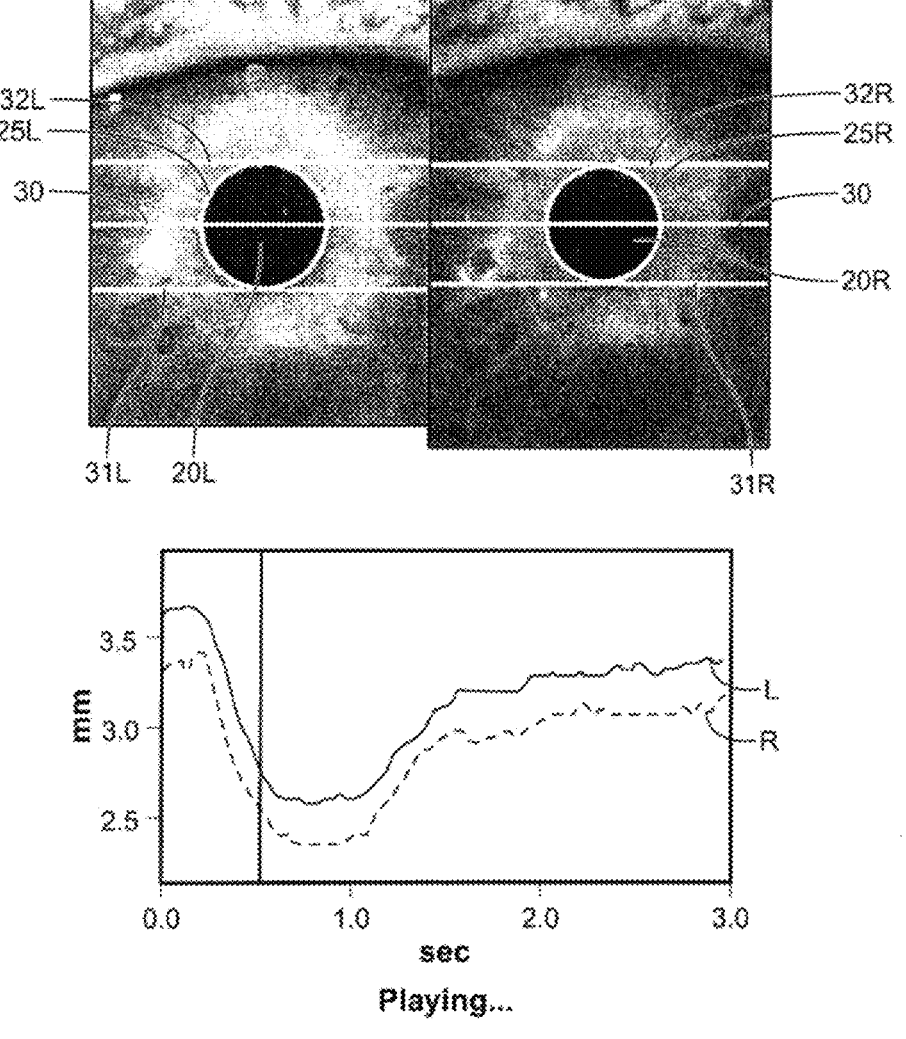
FIGS. 7-9 show different screen shots of the display of the Pupillometer depicted in FIG. 1 showing the left and right pupils of an individual aligned during video playback of pupillary response to a light stimulus along with a graphical representation of the pupillary response.
Figure 8:
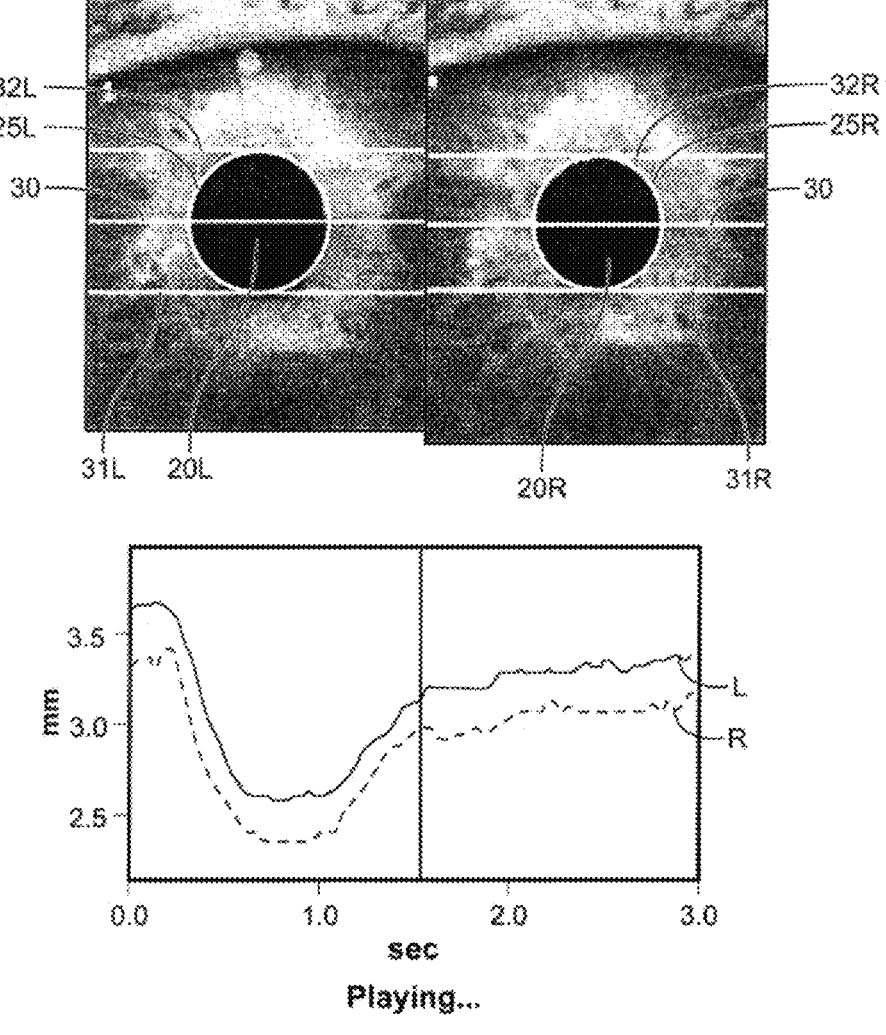
Figure 9:
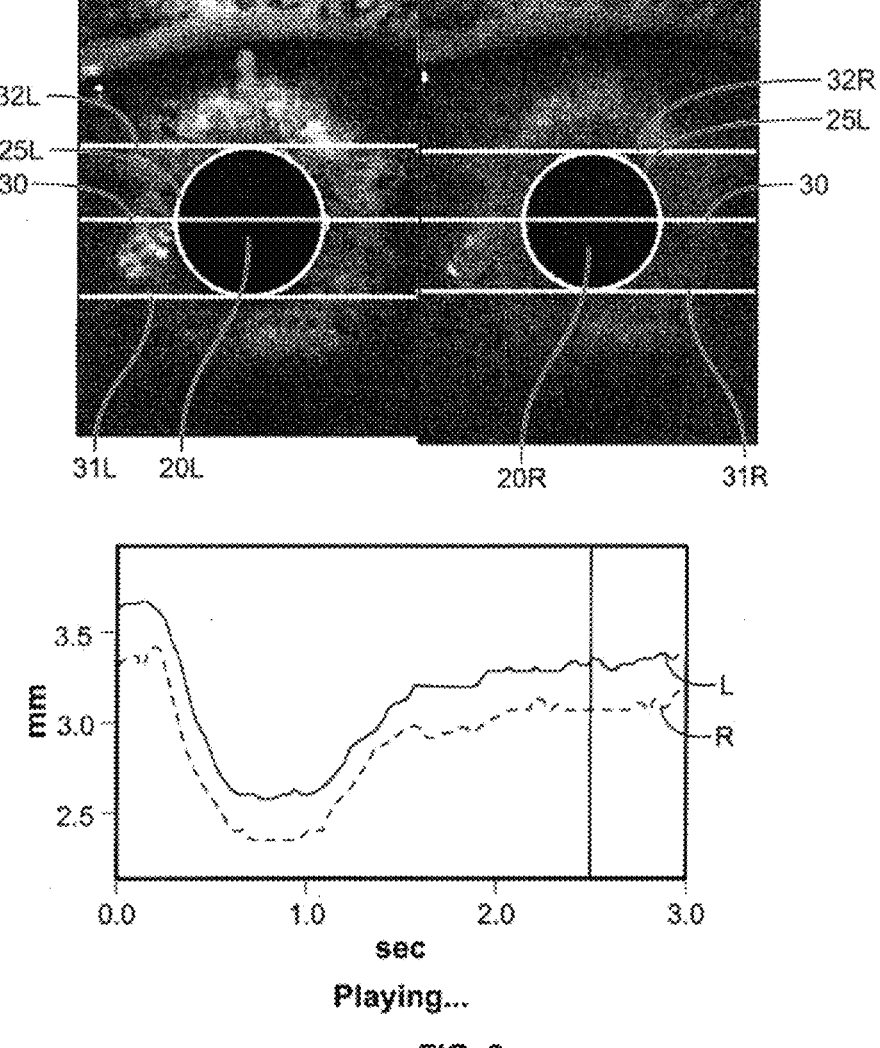

FIGS. 7-8 show a further feature of pupillometer 10. This further feature allows the user to see on the display 12 of pupillometer 10 not just synchronized and centered videos of the left and right pupil at the same time, as described above, but to view a graphical representation of the pupillary response of the left and right pupils superimposed together on a single graph. Images in FIG. 7 are taken at about 600 milliseconds after onset of the flash of light from pupillometer 10 (or from onset of video recording without a flash of light) as the pupils 20L and 20R are dilating. There is some minor difference as depicted in the graph below the images of the pupils 20L and 20R and as shown by the disconnection between sections 32L/31L and 32R/31R of the parallel lines. Images in FIG. 8 are taken at about 1.5 seconds after onset of the flash of light from pupillometer 10 (or from onset of video recording without a flash of light) as the pupils 20L and 20R are recovering back to their resting state. There is again some minor difference as depicted in the graph below the images of the pupils 20L and 20R and as shown by the disconnection between sections 32L/31L and 32R/31R of the parallel lines. Images in FIG. 9 are taken at about 2.6 seconds after onset of the flash of light from pupillometer 10 (or from onset of video recording without a flash of light) as the pupils 20L and 20R have fully dilated back to their resting position. Again, there is some minor difference as depicted in the graph below the images of the pupils 20L and 20R and as shown by the disconnection between sections 32L/31L and 32R/31R of the parallel lines. If viewed in rapid succession at 30 fps or even if slowed down to 10 fps, the operator of pupillometer 10 would be able to clearly see the difference in pupillary response between the left and right pupils to the flash of light from pupillometer 10 (or from onset of video recording without a flash of light). For example, the user can view the images one image set at a time and can control how long he or she wants to view the image set before manually forwarding or advancing to the next set of images or rewinding to the previous set of images. This can be done to compare the right pupil to the left pupil image set by image by set for each set of images taken during the procedure. The user can pause as long as he or she wants at a particular set of images to, for example, compare the difference between the right pupil and the left pupil in that set of images.

Methods for monitoring asymmetry in response between the left and right eye are also described herein. The methods are directed to whether or not an individual has either anisocoria and the level and severity of anisocoria, or asymmetry in response between the left and right eye to a stimulus, such as a light stimulus or other stimulus (or no stimulus at all). Determining whether a patient has aniso-coria or asymmetry in response can have diagnostic value.

In one aspect, a method for monitoring asymmetry in response to a stimulus between a left pupil and a right pupil of an individual involves the following steps, which can be performed with the aid of pupillometer 10 described above and illustrated in FIG. 1, or other diagnostic equipment. An operator, usually a medical professional, will position pup-illometer 10 with the headrest 16 against the patient's face around her left eye with the body of pupillometer 10 being perpendicular relative to the patient's axis of vision as shown in FIG. 2. It does not matter which eye is analyzed first as long as the data regarding whether the pupillary measurement is of the left eye or right eye is entered prior to taking the pupillary measurement. Pupillometer 10 is activated as described and it is used to record for a period of time y at a rate of x image frames per second a response of the left pupil to a flash of light (or simply recording the pupil at rest without a flash of light). When the measurement phase is activated, pupillometer 10 will issue a flash of light in the field of view of the left eye (or simply recording the pupil at rest without a flash of light) and will simultaneously begin recording images of the left pupil for a period of time y at a rate of x image frames per second as noted above. Recording will automatically stop after the period of time y has elapsed, and the images will be stored in the memory of pupillometer 10. The result of the recording is a video made up of a number of sequential image frames that when played back depict in a movie format the response of the pupil to the flash of light (or simply recording the pupil at rest without a flash of light). The same steps are then performed on the right eye and the image data of the right eye is also stored in the memory of pupillometer 10.

Now the operator can use the pupil comparison feature of pupillometer 10 to display on the display screen 12 of pupillometer 10 simultaneously the first set of image frames of the response of the left pupil and the second set of image frames of the response of the right pupil to the flash of light (or no stimulus at all). This will initiate the playback feature on the pupillometer 10. The pupil comparison feature of the pupillometer 10 will arrange the two sets of image frames on the display so that the center of the left pupil is aligned with the center of the right pupil on the display and the two sets of image frames are synchronized per frame starting from the first frame for each set with a straight line running from the center of both pupils. Stated somewhat differently, the two videos, the video of the left pupil and the video of the right pupil, will be aligned on the display 12 so that the center of the left pupil is aligned with the center of the right pupil on the display 12 and pupillometer 10 will then play the two videos simultaneously and in a synchronized fashion on the display screen 12.

To further enhance the ability of the operator to perceive any anisocoria, the comparison feature of pupillometer 10 draws a pair of parallel straight lines that extend from the perimeter of the left pupil to the perimeter of the right pupil in each image frame. The parallel lines have a first section and a second section, wherein in the first section the distance between the parallel lines is defined by the diameter of the left pupil for each image frame, and in the second section the distance between the parallel lines is defined by the diameter of the right pupil for each image frame. The color of the parallel lines in the first section can be different than the color of the parallel lines in the second section to make it easier for the operator to perceive any anisocoria. For example, the parallel lines in the first section can be green and the parallel lines in the second section can be red or vice versa. In addition, the user can view the images one image set at a time and can control how long he or she wants to view the image set before manually forwarding or advancing to the next set of images or rewinding to the previous set of images. This can be done to compare the right pupil to the left pupil image set by image by set for each set of images taken during the procedure. The user can pause as long as he or she wants at a particular set of images to, for example, compare the difference between the right pupil and the left pupil in that set of images.

In another embodiment, pupillometer 10 can be binocular (not shown) so that measurements of the left and right eye are taken simultaneously. Binocular Pupillometers, such as Neuroptics'® DP-1000 Pupillometer for Research are well known in the art.

While the invention is susceptible to various modifica-tions and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. A method of assessing a health condition of a mam-malian subject comprising:
    using a monocular handheld pupilometer to record images of a response of a left pupil of the subject to a first level of light stimulus;
    using said monocular handheld pupilometer to record images of a response of a right pupil of the subject to said same first level of light stimulus;
    using the pupilometer to provide an output comparing the response of the left eye to the response of the right eye; and
    determining whether there is asymmetry in pupillary response between the left eye and the right eye.

2. The method of claim 1, wherein the mammalian subject is a human.

3. The method of claim 2, wherein the output is a graphical representation of the pupillary response of the left and right pupils superimposed together on a single graph.

\* \* \* \* \*